US009834811B2

(12) United States Patent
Kavanagh et al.

(10) Patent No.: US 9,834,811 B2
(45) Date of Patent: *Dec. 5, 2017

(54) TRANSPOSON NUCLEIC ACIDS COMPRISING A CALIBRATION SEQUENCE FOR DNA SEQUENCING

(71) Applicant: Thermo Fisher Scientific Oy, Vantaa (FI)

(72) Inventors: Ian Kavanagh, Lucerne (CH); Laura-Leena Kiiskinen, Espoo (FI); Heli Haakana, Espoo (FI)

(73) Assignee: THERMO FISHER SCIENTIFIC OY, Vantaa (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/836,248

(22) Filed: Aug. 26, 2015

(65) Prior Publication Data

US 2016/0046980 A1     Feb. 18, 2016

Related U.S. Application Data

(63) Continuation of application No. 13/553,395, filed on Jul. 19, 2012, now Pat. No. 9,145,623.

(60) Provisional application No. 61/509,691, filed on Jul. 20, 2011.

(51) Int. Cl.
| | |
|---|---|
| *C12Q 1/68* | (2006.01) |
| *C12N 15/10* | (2006.01) |
| *C40B 40/08* | (2006.01) |
| *C40B 50/06* | (2006.01) |

(52) U.S. Cl.
CPC ....... *C12Q 1/6806* (2013.01); *C12N 15/1093* (2013.01); *C40B 40/08* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 6,593,113 | B1 | 7/2003 | Tenkanen et al. |
| 7,172,882 | B2 | 2/2007 | Savilahti et al. |
| 2005/0208616 | A1* | 9/2005 | Savilahti .............. C12N 15/902 435/69.1 |
| 2008/0318801 | A1 | 12/2008 | Leung |
| 2009/0022759 | A1* | 1/2009 | Burgert .................... C12N 7/00 424/199.1 |
| 2010/0120098 | A1 | 5/2010 | Grunenwald et al. |
| 2011/0287435 | A1 | 11/2011 | Grunenwald et al. |
| 2013/0017978 | A1 | 1/2013 | Kavanagh et al. |
| 2014/0202883 | A1 | 7/2014 | Nobile et al. |

FOREIGN PATENT DOCUMENTS

| | | |
|---|---|---|
| WO | 95/23875 | 9/1995 |
| WO | 2010/048605 | 4/2010 |

OTHER PUBLICATIONS

International Search Report PCT/EP2014/079473, dated Jun. 17, 2015, 5 pages.
Written Opinion of the International Searching Authority PCT2014/079473, dated Jun. 17, 2015, 9 pages.
Saariaho et al. Characteristics of MuA transposase-catalyzed processing of model transposon and DNA hairpin substrates. Nucleic Acids Research 24 (2006) 3139-3149.
Boeke, J. D. Transposable elements in *Saccharomyces cerevisiae*, *Mobile DNA*, 1989, pp. 335-374.
Craig, N. L. Transposon Tn7, *Current Topics in Microbiology and Immunology*, 1996, 204:27-48.
Devine, S. E. et al., Efficient integration of artificial transposons into plasmid targets in vitro: a useful tool for DNA mapping, sequencing and genetic analysis, *Nucleic Acids Research*, 1994, 22:18, pp. 3765-3772.
Goldhaber-Gordon et al. Sequence and Positional Requirements for DNA Sites in a Mu Transpososome, J. Biol Chem., vol. 277 (2002), pp. 7703-7712.
Haapa, S. et al., An efficient and accurate integration of mini-Mu transposons in vitro: a general methodology for functional genetic analysis and molecular biology applications, *Nucleic Acids Research*, 1999, 27:13, pp. 2777-2784.
Ichikawa, H. et al. In Vitro Transposition of Transposon Tn3. *The Journal of Biological Chemistry* 1990, 265:31, pp. 18829-18832.
Kaufman, P. D. et al., P. Element transposition in vitro proceeds by a cut-and-paste mechanism and uses GTP as a cofactor, *Cell*, 1992, 69:, pp. 27-39.
Kleckner N. et al., Tn10 and IS10 transposition and chromosome rearrangements: mechanism and regulation in vivo and in vitro, *Current Topics in Microbiology and Immunology*, 1996, 204:, pp. 49-82.
Lampe, D. J. et al., A purified mariner transposase is sufficient to mediate transposition in vitro, *The EMBO Journal*, 1996, 15:19, pp. 5470-5479.
Ohtsubo, E. et al., Bacterial insertion sequences, *Current Topics in Microbiology and Immunology*, 1996, 204:, pp. 1-26.
Park, B. T. et al., In Vitro transposition of Tn5, *J. Korean Soc. Microbiol.*, 1992, 27:4, pp. 381-389.
Savilahti, H. et al., Mu transpositional recombination: donor DNA cleavage and strand transfer in trans by the Mu transposase, *Cell*, 1996, 85:, pp. 271-280.
Savilahti, H. et al., The phage Mu transpososome core: DNA requirements for assembly and function, *EMBO Journal*, 1995, 14:19, pp. 4893-4903.

(Continued)

*Primary Examiner* — Nancy Treptow (57) ABSTRACT

Transposon nucleic acids comprising a transposon end sequence and a calibration sequence for DNA sequencing in the transposon end sequence. In one embodiment, the transposon end sequence is a Mu transposon end. A method for the generation of DNA fragmentation library based on a transposition reaction in the presence of a transposon end with the calibration sequence providing facilitated downstream handling of the produced DNA fragments, e.g., in the generation of sequencing templates.

**16 Claims, 11 Drawing Sheets
(2 of 11 Drawing Sheet(s) Filed in Color)**

(56) References Cited

OTHER PUBLICATIONS

Varmus, H. et al., Retroviruses, Mobile DNA, Berg D. E. and Howe M. eds. *American Society for Microbiology*, 1989, pp. 53-108.
Vos, J. C. et al., Transposase is the only nematode protein required for in vitro transposition of Tc1, *Genes & Development*, 1996, 10(6), pp. 755-761.

* cited by examiner

SEQUENCE LISTING

```
<160> NUMBER OF SEQ ID NOS: 9

<210> SEQ ID NO 1
<211> LENGTH: 50
<212> TYPE: DNA
<213> ORGANISM: Artificial Sequence
<220> FEATURE:
<223> OTHER INFORMATION: Bacteriophage Mu

<400> SEQUENCE: 1
gttttcgcat ttatcgtgaa acgctttcgc gttttcgtg cgccgcttca              50

<210> SEQ ID NO 2
<211> LENGTH: 50
<212> TYPE: DNA
<213> ORGANISM: Artificial Sequence
<220> FEATURE:
<223> OTHER INFORMATION: Modified Mu end sequence

<400> SEQUENCE: 2
gttttcgcat ttatcgtgaa acgctttcgc gttttcgtg cgccgctcag              50

<210> SEQ ID NO 3
<211> LENGTH: 50
<212> TYPE: DNA
<213> ORGANISM: Artificial Sequence
<220> FEATURE:
<223> OTHER INFORMATION: Modified Mu end sequence

<400> SEQUENCE: 3
```

```
gttttcgcat ttatcgtgaa acgctttcgc gttttcgtg cgccgcgtca         50

<210> SEQ ID NO 4
<211> LENGTH: 50
<212> TYPE: DNA
<213> ORGANISM: Artificial Sequence
<220> FEATURE:
<223> OTHER INFORMATION: Modified Mu end sequence

<400> SEQUENCE: 4
gttttcgcat ttatcgtgaa acgctttcgc gttttcgtg cgccgctgca         50

<210> SEQ ID NO 5
<211> LENGTH: 50
<212> TYPE: DNA
<213> ORGANISM: Artificial Sequence
<220> FEATURE:
<223> OTHER INFORMATION: Modified Mu end sequence

<400> SEQUENCE: 5
gttttcgcat ttatcgtgaa acgctttcgc gttttcgtg cgtcagttca         50

<210> SEQ ID NO 6
<211> LENGTH: 50
<212> TYPE: DNA
<213> ORGANISM: Artificial Sequence
<220> FEATURE:
<223> OTHER INFORMATION: Modified Mu end sequence

<400> SEQUENCE: 6
gttttcgcat ttatcgtgaa acgctttcgc gttttcgtc agccgcttca         50

<210> SEQ ID NO 7
<211> LENGTH: 50
<212> TYPE: DNA
<213> ORGANISM: Artificial Sequence
<220> FEATURE:
<223> OTHER INFORMATION: transposon

<400> SEQUENCE: 7
tgaagcggcg cacgaaaaac gcgaaagcgt ttcacgataa atgcgaaaac         50

<210> SEQ ID NO 8
<211> LENGTH: 50
<212> TYPE: DNA
<213> ORGANISM: Artificial Sequence
<220> FEATURE:
<223> OTHER INFORMATION: transposon

<400> SEQUENCE: 8
caaaagcgta aatagcactt tgcgaaagcg caaaaagcac gaggcgaagt         50

<210> SEQ ID NO 9
<211> LENGTH: 50
<212> TYPE: DNA
<213> ORGANISM: Artificial Sequence
<220> FEATURE:
<223> OTHER INFORMATION: transposon

<400> SEQUENCE: 9
acttcgccgc gtgcttttg cgctttcgca aagtgctatt tacgcttttg         50
```

TRANSPOSON NUCLEIC ACIDS COMPRISING A CALIBRATION SEQUENCE FOR DNA SEQUENCING

This application is a continuation of U.S. patent application Ser. No. 13/553,395 filed Jul. 19, 2012, now issued U.S. Pat. No. 9,145,623 and claims priority to U.S. Provisional Application Ser. No. 61/509,691 filed Jul. 20, 2011, each of which are expressly incorporated by reference herein in their entirety.

The invention relates to the field of high throughput multiplex DNA sequencing. The invention is directed to transposon nucleic acids comprising a transposon end sequence and a calibration sequence for DNA sequencing in the transposon end sequence. In one embodiment, this transposon end sequence is a Mu transposon end. The invention is also directed to a method for generation of a DNA fragmentation library based on a transposition reaction in the presence of a transposon end with the calibration sequence, providing facilitated downstream handling of the produced DNA fragments, e.g., in the generation of sequencing templates.

BACKGROUND

"DNA sequencing" generally refers to methodologies aiming to determine the primary sequence information in a given nucleic acid molecule. Traditionally, Maxam-Gilbert and Sanger sequencing methodologies have been applied successfully for several decades, as well as a pyrosequencing method. However, these methodologies have been difficult to multiplex, as they require a wealth of labor and equipment time, and the cost of sequencing is excessive for entire genomes. These methodologies required each nucleic acid target molecule to be individually processed, the steps including, e.g., subcloning and transformation into E. coli bacteria, extraction, purification, amplification, and sequencing reaction preparation and analysis.

So called "next-generation" technologies or "massive parallel sequencing" platforms allow millions of nucleic acid molecules to be sequenced simultaneously. The methods rely on sequencing-by-synthesis approach, while certain other platforms are based on sequencing-by-ligation technology. Although very efficient, all of these new technologies rely on multiplication of the sequencing templates. Thus, for each application, a pool of sequencing templates needs to be produced. A major advancement for template generation was the use of in vitro transposition technology. The earliest in vitro transposition-assisted sequencing template generation methodology (Tenkanen U.S. Pat. No. 6,593,113) discloses a method in which the transposition reaction results in fragmentation of the target DNA, and the subsequent amplification reaction is carried out in the presence of a fixed primer complementary to the known sequence of the target DNA and a selective primer having a complementary sequence to the end of a transposon DNA.

In vitro transposition methodology has also been applied to "next generation" sequencing platforms. Grunenwald (U.S. Patent Application 20100120098) disclose methods using a transposase and a transposon end for generating extensive fragmentation and 5'-tagging of double-stranded target DNA in vitro. The method is based on the use of a DNA polymerase for generating 5'- and 3'-tagged single-stranded DNA fragments after fragmentation without performing a PCR amplification reaction.

Many "next-generation" sequencing instruments require a specific calibration sequence to be read first as a part of the sequence to be analyzed (e.g. ion torrent PGM and Roche 454 Genome Sequencer FLX System). This calibration sequence has known bases in particular order and it calibrates the instrument so that it is capable of differentiating the signal generated from different bases during the DNA sequencing reaction. It is necessary that each of the sequencing templates comprises this calibration sequence.

Methods that facilitate the downstream handling of the fragmented DNA obtained from the transposition step are needed.

SUMMARY

The invention is related to the modification of a transposon end sequence so that it includes a calibration sequence for DNA sequencing. When the transposon end sequence is inserted into the target DNA in the fragmentation reaction, the calibration sequence is simultaneously incorporated into the target sequence.

A modified transposon nucleic acid comprising a transposon end sequence and an engineered calibration sequence for DNA sequencing in the transposon end sequence, and a kit for DNA sequencing containing the modified transposon nucleic acid.

An in vitro method for generating a DNA library by incubating a transposon complex comprising a transposon nucleic acid and a transposase with a target DNA of interest under conditions for carrying out a transposition reaction, where the transposon nucleic acid comprises a transposon end sequence recognizable by the transposase, where the transposon end sequence comprises a calibration sequence for DNA sequencing, and where the transposition reaction results in fragmentation of the target DNA and incorporation of the transposon end into the 5' end of the fragmented target DNA.

BRIEF DESCRIPTION OF THE DRAWINGS

The patent or application file contains at least one drawing executed in color. A Petition under 37 C.F.R. §1.84 requesting acceptance of the color drawing is being filed separately. Copies of this patent or patent application publication with color drawing(s) will be provided by the Office upon request and payment of the necessary fee.

DETAILED DESCRIPTION

The terms "calibration sequence" or "key sequence" as used herein generally refer to a nucleic acid sequence that can be used to calibrate a DNA sequencing system. Thus, in embodiments, the particular bases, the order of the bases, and the number of bases that are present in a calibration sequence depends on the requirements of a particular DNA sequencing system.

In one embodiment, the calibration sequence is a four-nucleotide-long nucleic acid sequence of the four known bases (A, T, C and G) in particular order incorporated into target DNA to be sequenced. The calibration sequence calibrates the sequencing instrument for each sample so that it is capable of differentiating the signal generated from different bases during the DNA sequencing reaction. For example, sequences TCAG, GTCA and TGCA can be used as calibration sequences. However, the four bases could be presented in the calibration sequence in any possible order. In embodiments, the calibration sequence may be longer than four nucleotides, e.g., the calibration sequence may be five, six, seven, eight, nine, ten, or more nucleotides long. The calibration sequence may also comprise bases in addition to, or in place of, the four known bases A, T, G, and C. For example, the calibration sequence may contain derivatized and/or artificial nucleotide bases; such modified bases are known to one skilled in the art.

The term "transposon", as used herein, refers to a nucleic acid segment that is recognized by a transposase or an integrase enzyme and is an essential component of a functional nucleic acid-protein complex (i.e., a transpososome) capable of transposition. In one embodiment, a minimal nucleic acid-protein complex capable of transposition in a Mu transposition system comprises four MuA transposase protein molecules and a pair of Mu transposon end sequences that are able to interact with MuA (FIG. 6) where the DNA sequences of the fragments from the transposition reaction are, e.g., SEQ ID NO: 1 . . . Insert from Target DNA . . . gap SEQ ID NO: 7

Figure 6:
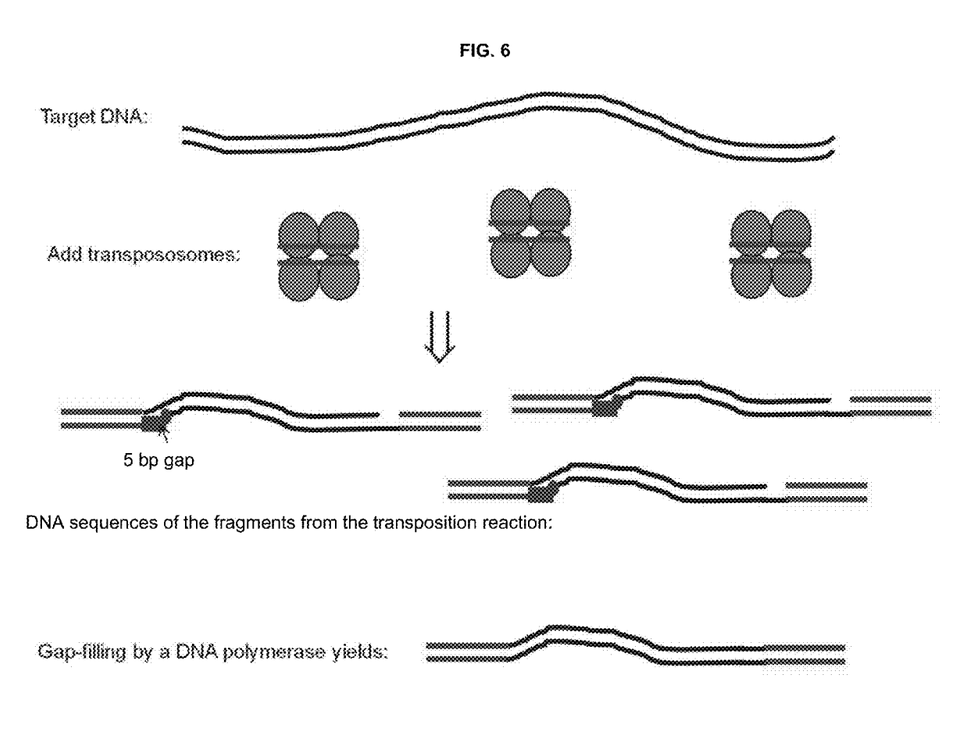
FIG. 6 shows a transposition reaction with Mu transposon end sequences on target DNA.
Figure 7:
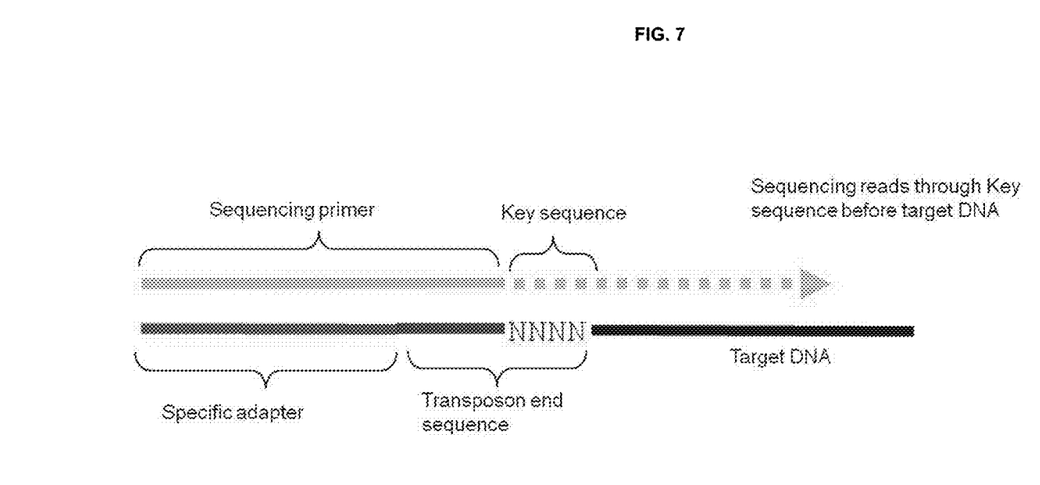
FIG. 7 shows downstream sequencing reaction with target DNA comprising an incorporated transposon end with calibration sequence.

SEQ ID NO: 8 gap . . . SEQ ID NO: 9 and showing the product after gap-filling by a DNA polymerase.

The term "transposase" as used herein refers to an enzyme that is a component of a functional nucleic acid-protein complex capable of transposition and which is mediating transposition. The term "transposase" also refers to integrases from retrotransposons or of retroviral origin.

A "transposition reaction" as used herein refers to a reaction where a transposon inserts into a target nucleic acid. Primary components in a transposition reaction are a transposon and a transposase or an integrase enzyme. The method and materials of the invention are exemplified by employing in vitro Mu transposition (Haapa et al. 1999 and Savilahti et al. 1995). Other transposition systems can be used, e.g., Ty1 (Devine and Boeke, 1994, and WO 95/23875), Tn7 (Craig, 1996), Tn 10 and IS 10 (Kleckner et al. 1996), Mariner transposase (Lampe et al., 1996), Tcl (Vos et al., 1996, 10(6), 755-61), Tn5 (Park et al., 1992), P element (Kaufman and Rio, 1992) and Tn3 (Ichikawa and Ohtsubo, 1990), bacterial insertion sequences (Ohtsubo and Sekine, 1996), retroviruses (Varmus and Brown 1989), and retrotransposon of yeast (Boeke, 1989).

A "transposon end sequence" as used herein refers to the nucleotide sequences at the distal ends of a transposon. The transposon end sequences are responsible for identifying the transposon for transposition; they are the DNA sequences the transpose enzyme requires to form a transpososome complex and to perform a transposition reaction. For MuA transposase, this sequence is 50 bp long (SEQ ID NO. 1) described by Goldhaber-Gordon et al., J Biol Chem. 277 (2002) 7703-7712, which is hereby incorporated by reference in its entirety. A transposable DNA of the present invention may comprise only one transposon end sequence. The transposon end sequence in the transposable DNA sequence is thus not linked to another transposon end sequence by a nucleotide sequence, i.e., the transposable DNA contains only one transposase binding sequence. Thus, the transposable DNA comprises a "transposon end" (e.g., Savilahti et al., 1995).

A "transposase binding sequence" or "transposase binding site" as used herein refers to the nucleotide sequences that are always within the transposon end sequence where a transposase specifically binds when mediating transposition. The transposase binding sequence may comprise more than one site for binding transposase subunits.

A "transposon joining strand" or "joining end" as used herein means the end of that strand of the double-stranded transposon DNA that is joined by the transposase to the target DNA at the insertion site.

The term "adaptor" or "adaptor tail" as used herein refers to a non-target nucleic acid component, generally DNA, that provides a means of addressing a nucleic acid fragment to which it is joined. For example, in embodiments, an adaptor comprises a nucleotide sequence that permits identification, recognition, and/or molecular or biochemical manipulation of the DNA to which the adaptor is attached (e.g., by providing a site for annealing an oligonucleotide, such as a primer for extension by a DNA polymerase, or an oligonucleotide for capture or for a ligation reaction).

Many "next-generation" sequencing instruments (e.g. ion torrent PGM and Roche 454 Genome Sequencer FLX System) require a specific calibration sequence to be read first as a part of the sequence to be analyzed. Because the in vitro transposition technology is already used to fragment target DNA for sequencing, the disclosed method provides transposon end sequences that include the calibration sequence. In this way, the calibration sequence would be incorporated to the target DNA during the fragmentation step. To reduce unusable sequence reads, this calibration sequence may be designed as close to the 3' inserted end of the transposon end (i.e., the joining end) as possible.

The MuA transposase recognizes a certain transposon end sequence of 50 bp (SEQ ID NO:1) but tolerates some variation at certain positions (Goldhaber-Gordon et al., J Biol Chem. 277 (2002) 7703-7712). Various options for including a calibrator sequence into the transposon end were designed.

In one embodiment, a modified transposon nucleic acid comprising a transposon end sequence and an engineered calibration sequence for DNA sequencing in the transposon end sequence is provided. The transposon end sequence may be a Mu transposon end sequence, and the Mu transposon end sequence may be any of SEQ ID NOS: 3-6. In one embodiment, the Mu transposon end sequence is SEQ ID NO: 5.

In one embodiment, a modified transposon nucleic acid comprising a transposon end sequence and an engineered calibration sequence for DNA sequencing in the transposon end sequence is provided, where the transposon end sequence further contains an engineered cleavage site. An engineered cleavage site in the transposon end sequence can be useful for removing parts of the transposon end sequence from the fragmented DNA, which improves downstream amplification (e.g., by reducing intramolecular loop structures, as a result of less complementary sequence) or reduces the amount of transposon end sequence that would be read during sequencing (e.g., single molecule sequencing). In embodiments, the engineered cleavage site may be the incorporation of a uracil base or a restriction site. Modified transposon end sequences comprising an engineered calibration sequence for DNA sequencing and optionally an uracil base or an additional restriction site can be produced, e.g., by regular oligonucleotide synthesis.

In one embodiment, an in vitro method for generating a DNA library is provided. The method incubates a transposon complex comprising a transposon nucleic acid and a transposase with a target DNA of interest under conditions for carrying out a transposition reaction. Transposon nucleic acid comprises a transposon end sequence that is recognizable by the transposase, and where the transposon end sequence comprises a calibration sequence for DNA sequencing. The transposition reaction results in fragmentation of the target DNA, and incorporates the transposon end into the 5' end of the fragmented target DNA.

In one embodiment, the method further comprises the step of amplifying the fragmented target DNA in an amplification reaction using a first and second oligonucleotide primer complementary to the transposon end in the 5' ends of the fragmented target DNA. The first and second primer optionally comprise 5' adaptor tails.

In one embodiment, the method further comprises the step of contacting the fragments of target DNA comprising the transposon end at the 5' ends of the fragmented target DNA with DNA polymerase having 5'-3' exonuclease or strand displacement activity, so that fully double-stranded DNA molecules are produced from the fragments of target DNA. This step is used to fill the gaps generated in the transposition products in the transposition reaction. The length of the gap is characteristic to a certain transposition enzyme, e.g., for MuA the gap length is 5 nucleotides.

To prepare the transposition products for downstream steps, such as polymerase chain reaction (PCR), the method may comprise the further step of denaturating the fully double-stranded DNA molecules to produce single stranded DNA for use in the amplification reaction.

In one embodiment, the transposition system used in the method is based on MuA transposase enzyme. For the method, one can assemble in vitro stable but catalytically inactive Mu transposition complexes in conditions devoid of $Mg^{2+}$ as disclosed in Savilahti et al., 1995 and Savilahti and Mizuuchi, 1996. In principle, any standard physiological buffer not containing $Mg^{2+}$ is suitable for assembly of the inactive Mu transposition complexes. In one embodiment, the in vitro transpososome assembly reaction may contain 150 mM Tris-HCl pH 6.0, 50% (v/v) glycerol, 0.025% (w/v) Triton X-100, 150 mM NaCl, 0.1 mM EDTA, 55 nM transposon DNA fragment, and 245 nM MuA. The reaction volume may range from about 20 µl to about 80 µl. The reaction is incubated at about 30° C. for about 0.5 hours to about four hours. In one embodiment, the assembly reaction is incubated for two hours at about 30° C. $Mg^{2+}$ is added for activation.

In case the transposon end sequence comprises an engineered cleavage site, the method can comprise a further step of incubating the fragmented target DNA with an enzyme specific to the cleavage site so that the transposon ends incorporated to the fragmented target DNA are cleaved at the cleavage site. The cleaving enzyme may be an N-glycosylase or a restriction enzyme, such as uracil-N-glycosylase or a methylation specific restriction enzyme, respectively.

In one embodiment, the 5' adaptor tail of the first and/or second PCR primer(s) used in the method comprise one or more of the following groups: an amplification tag, a sequencing tag, and/or a detection tag.

The amplification tag is a nucleic acid sequence providing specific sequence complementary to an oligonucleotide primer to be used in the subsequent rounds of amplification. For example, the sequence may be used for facilitating amplification of the nucleic acid obtained. Examples of detection tags are fluorescent and chemiluminescent dyes, a green fluorescent protein, and enzymes that are detectable in the presence of a substrate, e.g., an alkaline phosphatase with NBT plus BCIP, or a peroxidase with a suitable substrate. By using different detection tags, i.e. barcodes, sequences from multiple samples can be sequenced in the same instrument run and identified by the sequence of the detection tag. Examples are Illumina's index sequences in TruSeq DNA Sample Prep Kits, or Molecular barcodes in Life Technologies' SOLiD™ DNA Barcoding Kits.

The sequencing tag provides a nucleic acid sequence permitting the use of the amplified DNA fragments obtained from step c) as templates for next-generation sequencing. For example, the sequencing tag may provide annealing sites for sequencing by hybridization on a solid phase. Such sequencing tag may be Roche 454A and 454B sequencing tags, Applied Biosystems' SOLiD™ sequencing tags, ILLUMINA™ SOLEXA™ sequencing tags, the Pacific Biosciences' SMRT™ sequencing tags, Pollonator Polony sequencing tags, and the Complete Genomics sequencing tags.

The detection tag comprises a sequence or a detectable chemical or biochemical moiety for facilitating detection of the nucleic acid obtained from the amplification step.

In one embodiment, a kit for use in DNA sequencing is provided. The kit comprises at least a transposon nucleic acid comprising transposon end sequence and an engineered calibration sequence for DNA sequencing in the transposon end sequence. In one embodiment, the transposon nucleic acid is a Mu transposon end sequence. In one embodiment, the Mu transposon end sequence is selected from SEQ ID NOS: 3-6. In one embodiment, the Mu transposon end sequence is SEQ ID NO:5. In one embodiment, the transposon nucleic acid further comprises an engineered cleavage site. The kit may also comprise additional components, e.g., buffers for performing transposition reaction, buffers for DNA sequencing, control DNA, transposase enzyme, and DNA polymerase. The kit can be packaged in a suitable container with instructions for using the kit.

The publications and other materials used herein to illuminate the background of the invention, and in particular, to provide additional details with respect to its practice, are incorporated herein by reference. The present invention is further described in the following examples, which are not intended to limit the scope of the invention.

EXAMPLE 1

Native Sequence of the Inserted Strand of MuA Recognition Transposon End

In various embodiments, a calibration sequence is four bases long and contains each of the four bases (A, T, G, C) sequentially in a row but in any order. The native MuA recognition sequence only contains these at underlined positions which are far from the 3'-end.

(SEQ ID NO: 1)
GTTTTC<u>GCATTT</u>ATCGTGAAACGCTTTCGCGTTTTTCGTGCGCCGCTTCA

If these sequences were used as calibrators, a minimum of 34 bases of the inserted transposon sequence would have to be read in every target fragment before reaching the sequence of interest, wasting sequencing reagents and instrument run time. The accuracy of sequence reading also gradually decreases after each cycle, so the best possible accuracy would always be "wasted" on reading the transposon end sequence. In addition, the bases in the "native calibrator sequences" are not necessarily in the preferred order, as defined by the instruments' requirements. That is why the MuA recognition sequence needs to be modified near the 3'-end in order to be used in library generation for instruments that require a calibration sequence. Other transposons, such as the native Tn5 recognition transposon sequence, do not contain the four bases in a row anywhere in its sequence.

Figure 1:
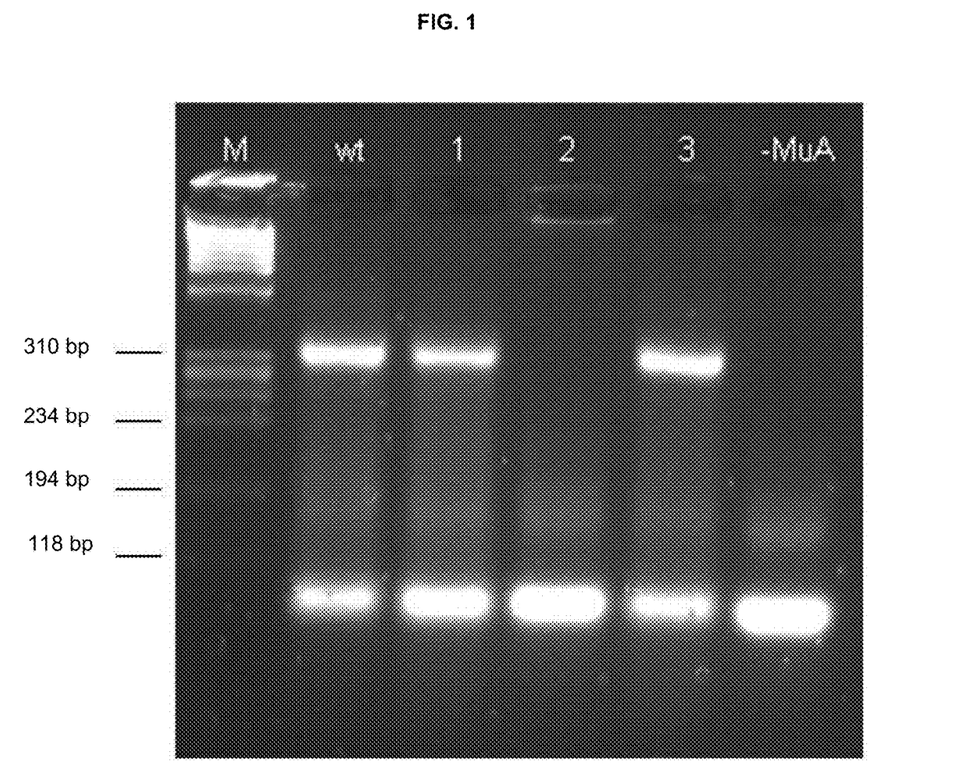
FIG. 1 is a gel showing a complex formation with MuA transposase and varying transposon end sequences.

When the transposon end sequence and MuA transposase were incubated together in a suitable buffer, they formed transpososome complexes (FIG. 1). The higher molecular weight DNA band of about 300 bp represents transposon end DNA bound to transpososome complexes (mobility in the gel electrophoresis is retarded due to protein binding) and the smaller DNA band (50 bp) is the free transposon DNA, i.e. not complexed by MuA. M: Molecular weight marker. wt: Native MuA transposon end +MuA transposase. 1: Transposon end of SEQ ID NO:4. 2: Transposon end of SEQ ID NO:2. 3: Transposon end of SEQ ID NO:3. –MuA: Control reaction with native MuA transposon end DNA sequence (SEQ ID NO: 1) without MuA transposase.

Figure 2A:
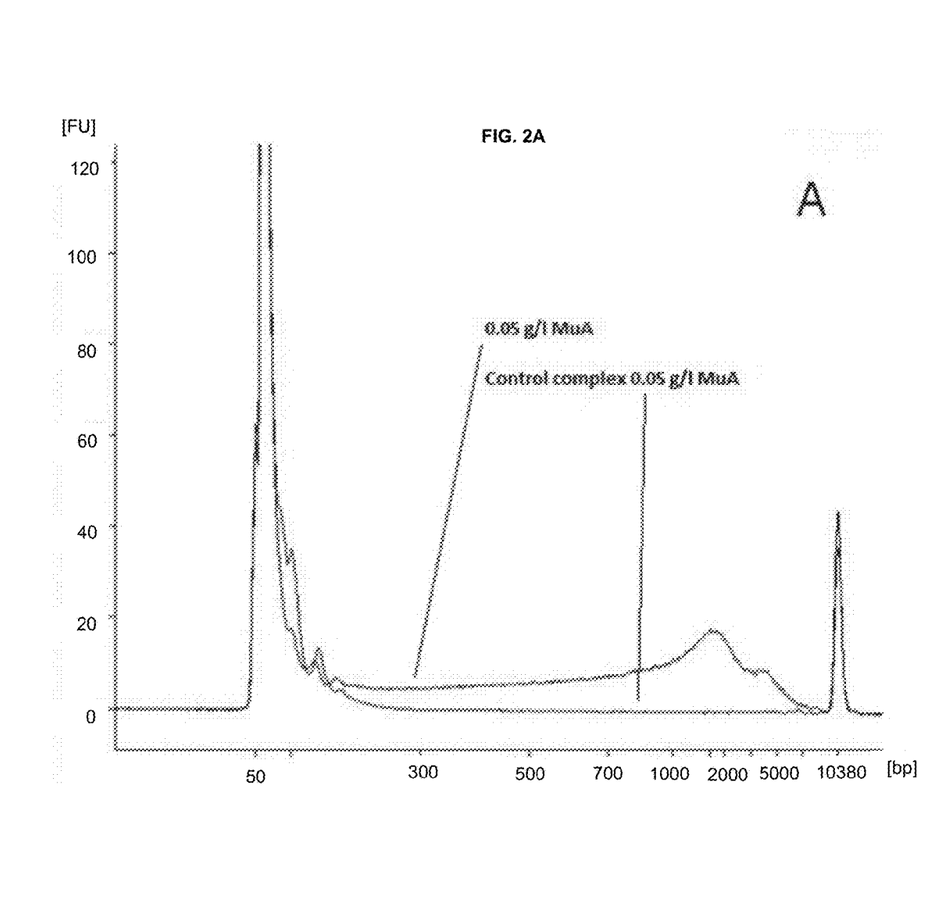
FIGS. 2A-C show human genomic DNA fragmented with different amounts of transpososome complexes.
Figure 2B:
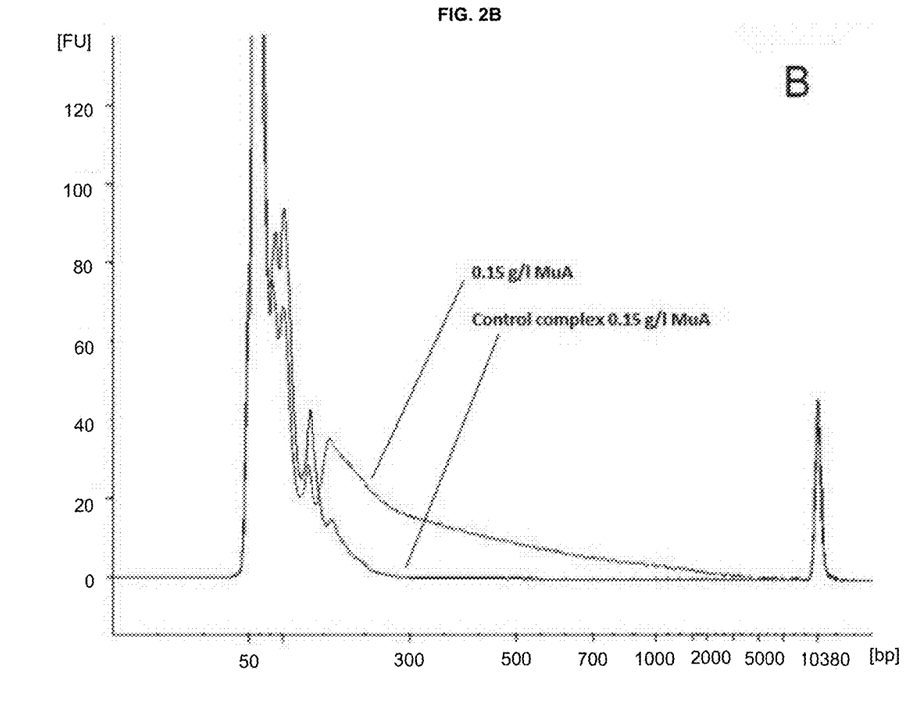
Figure 2C:
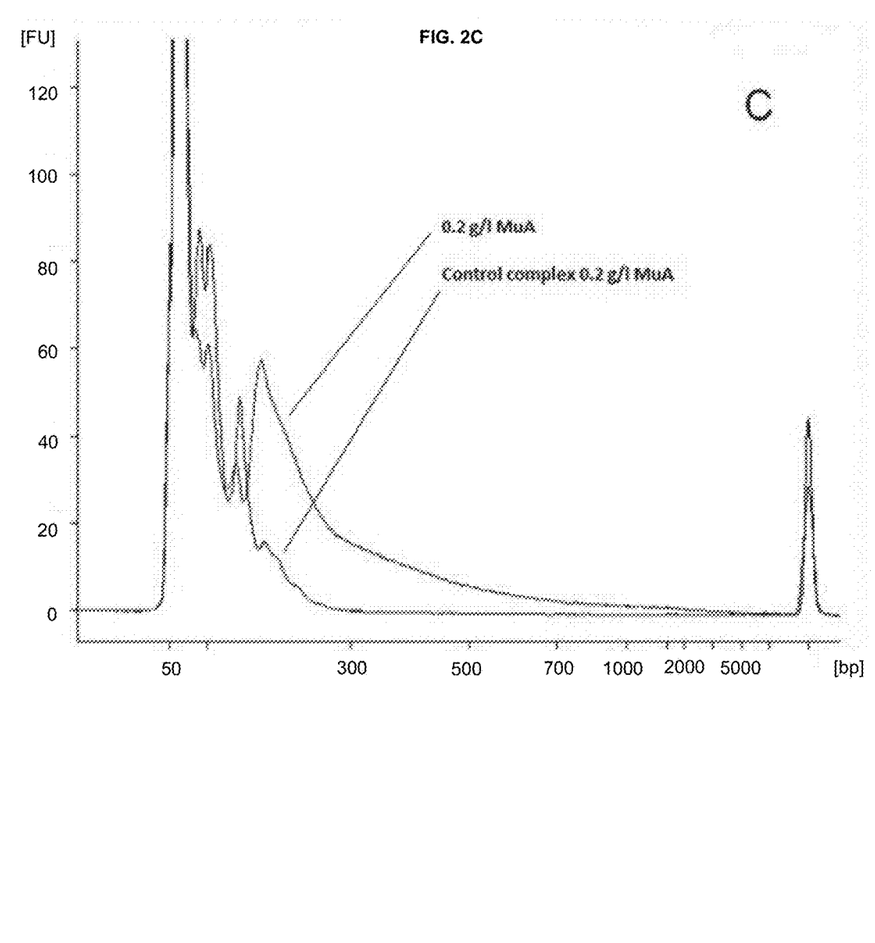

When these complexes (formed using wild-type MuA transposon end DNA and MuA transposase) were incubated with target DNA, the transposon sequences were inserted into DNA and the target DNA was fragmented, as shown in FIGS. 2A-C. FIG. 2A: 0.05 g/L MuA in the fragmentation reaction. FIG. 2B: 0.15 g/l MuA. FIG. 2C: 0.2 g/l MuA, gDNA fragmented with MuA. Control contains MuA complexes but no gDNA.

TABLE 1

Composition of the complex formation reaction in FIG. 1. The following components of the complex formation reaction were incubated for one hour at 30° C.

| MuA transposase | 0.44 | g/l |
| Transposon DNA | 3.0 | μM |
| Tris-HCl pH 8 | 120.42 | mM |
| HEPES pH 7.6 | 2.6 | mM |
| EDTA | 1.05 | mM |
| DTT | 0.10 | mM |
| NaCl | 102.1 | mM |
| KCl | 52 | mM |
| Triton X-100 | 0.05 | % |
| glycerol | 12.08 | % |
| DMSO | 10 | % |

Different amounts of the complex were incubated with human genomic DNA at 30° C. for one hour (Table 2), and each reaction was replicated eight times. The replicates were combined after the fragmentation, DNA was purified with QIAGEN MinElute PCR Purification Kit, and analyzed with Agilent 2100 Bioanalyzer instrument (FIG. 2).

TABLE 2

Example of final composition of the fragmentation reaction. For the fragmentation reaction, the MuA transposon and transposon DNA concentrations were varied in different experiments, whereas the concentration of other components was kept constant.

| MuA transposon | 0.05 | g/l |
| Transposon DNA | 0.341 | μM |
| gDNA | 100 | ng |
| Tris-HCl pH 8 | 40 | mM |

TABLE 2-continued

Example of final composition of the fragmentation reaction. For the fragmentation reaction, the MuA transposon and transposon DNA concentrations were varied in different experiments, whereas the concentration of other components was kept constant.

| EDTA | 0.33 | mM |
| NaCl | 100 | mM |
| MgCl₂ | 10 | mM |
| Triton X-100 | 0.05 | % |
| glycerol | 10 | % |
| DMSO | 3.3 | % |

EXAMPLE 2

Changing of the Mu 3'-End to Include the Current Ion Torrent Key Sequence (TCAG)

(SEQ ID NO: 2)
GTTTTCGCATTTATCGTGAAACGCTTTCGCGTTTTTCGTGCGCCGCTCAG

This transposon end sequence was tested. MuA transposase did not form complexes with this sequence and thus there was no transposition activity (see FIG. 1).

EXAMPLE 3

Converting the Fourth T of Mu End Sequence to G (Counting from the 3'-End) to Yield GTCA Key (SEQ ID NO: 3)
GTTTTCGCATTTATCGTGAAACGCTTTCGCGTTTTTCGTGCGCCGCGTCA This was tested for transposition activity and MuA transposase formed complexes with this sequence and was also active (FIG. 1).

EXAMPLE 4

Converting the Third T of Mu End Sequence to G to Yield TGCA Key (SEQ ID NO: 4)
GTTTTCGCATTTATCGTGAAACGCTTTCGCGTTTTTCGTGCGCCGCTGCA This was tested for transposition activity and MuA transposase formed complexes with this sequence and was also active (FIG. 1).

EXAMPLE 5

Figure 3:
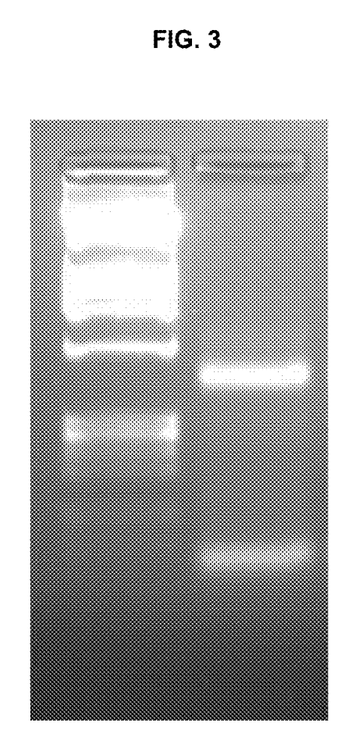
FIG. 3 is a gel showing a complex formation similar to FIG. 1, but with transposon end of SEQ ID NO: 5.
Figure 4A:
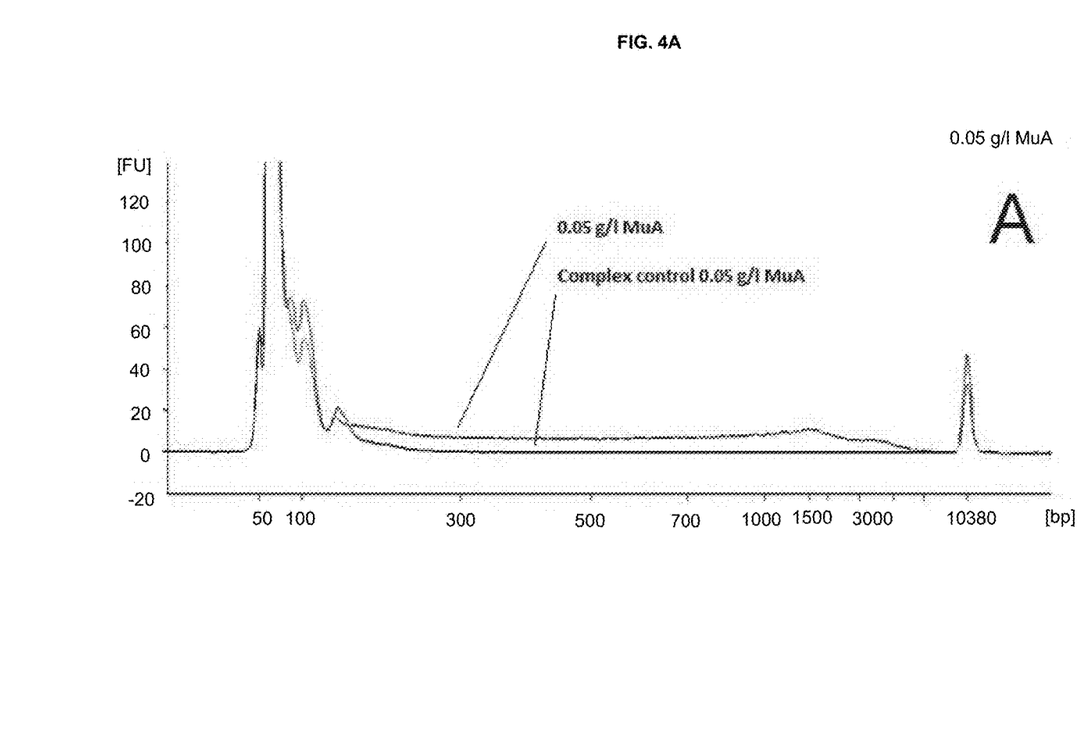
FIGS. 4A-B are similar to FIGS. 2A-C, but with transposon end of SEQ ID NO: 5.
Figure 4B:
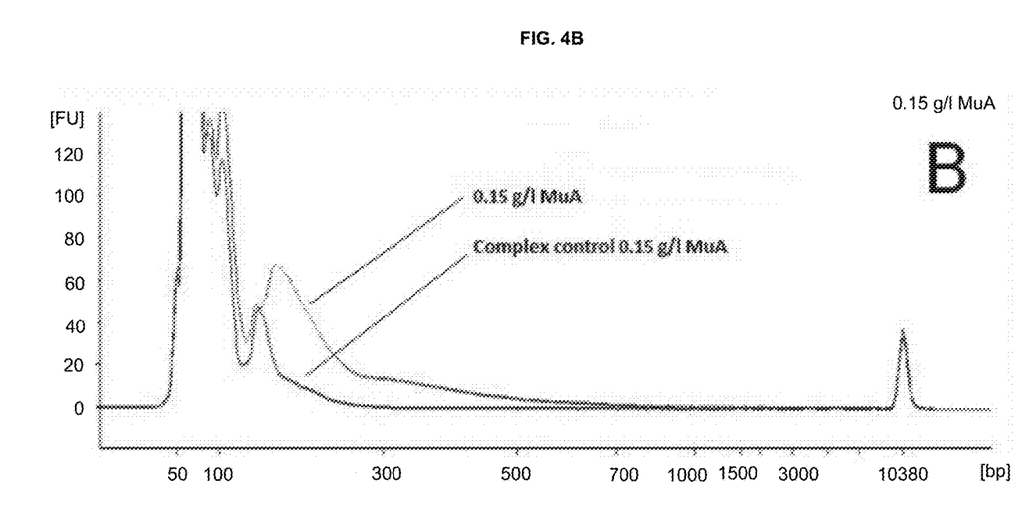

Modification of the 5th, 6th, and 8th Bases of Mu End Sequence into G, A, and T, Respectively, to Yield the Current Ion Torrent Key (SEQ ID NO: 5)
GTTTTCGCATTTATCGTGAAACGCTTTCGCGTTTTTCGTGCGTCAGTTCA This transposon end sequence worked well with MuA transposase in complex formation, as shown in FIG. 3, which shows complex formation similar to FIG. 1, but with transposon end of SEQ ID NO: 5, and in fragmentation, as shown in FIG. 4, which is similar to FIG. 2, but with transposon end of SEQ ID NO: 5, i.e. showing human genomic DNA fragmented with different amounts of transpososome complexes. FIG. 4A: 0.05 g/L MuA in the fragmentation reaction. FIG. 4B: 0.15 g/l MuA, with gDNA fragmented with MuA and control that contains MuA complexes but no gDNA.

EXAMPLE 6

Modification of the 10th, and 11th bases of Mu end sequence into A and C, respectively

```
                                              (SEQ ID NO: 6)
GTTTTCGCATTTATCGTGAAACGCTTTCGCGTTTTTCGTCAGCCGCTTCA
```

Figure 5A:
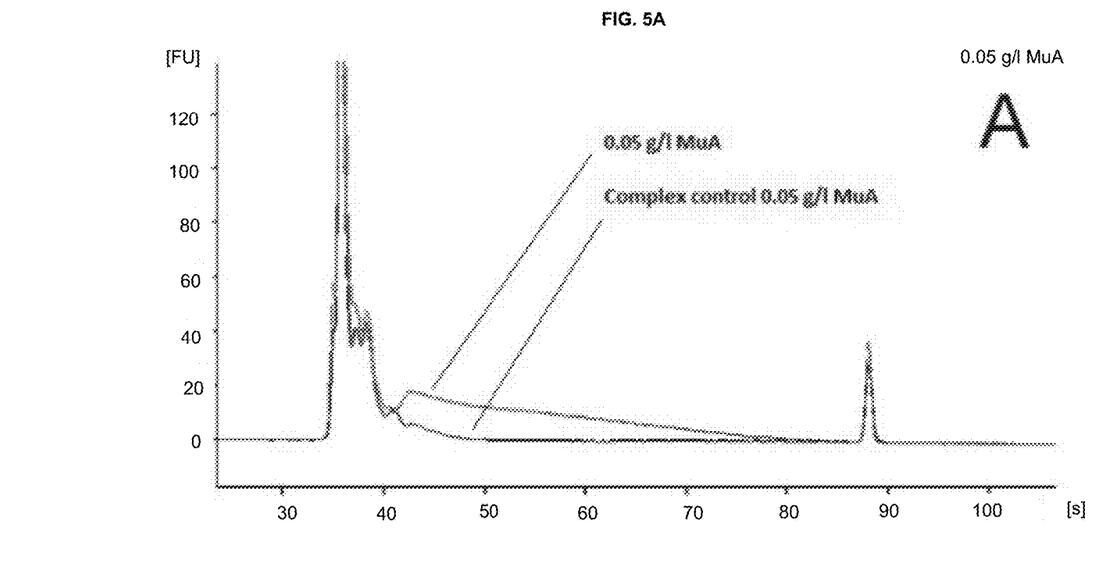
FIGS. 5A-B are similar to FIGS. 2A-C, but with transposon end of SEQ ID NO: 6.
Figure 5B:
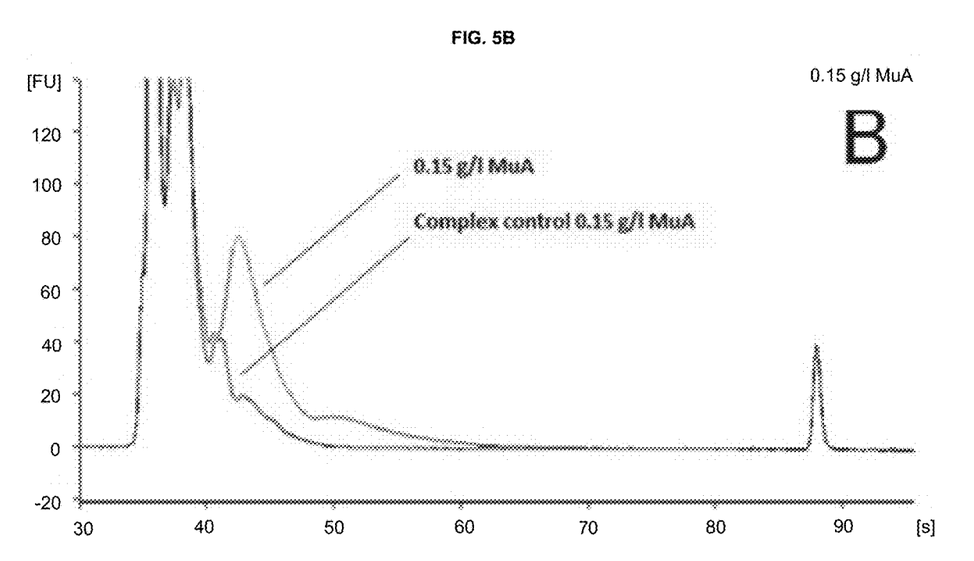

This transposon end sequence worked well with MuA transposase in complex formation and in fragmentation, as shown in FIG. 5, which is similar to FIG. 2, but with transposon end of SEQ ID NO: 6, i.e. showing human genomic DNA fragmented with different amounts of transpososome complexes. FIG. 5A: 0.05 g/L MuA in the fragmentation reaction. FIG. 5B: 0.15 g/l MuA, with gDNA fragmented with MuA and control that contains MuA complexes but no gDNA.

REFERENCES

Boeke J. D. 1989. Transposable elements in *Saccharomyces cerevisiae* in Mobile DNA.

Craig N. L. 1996. Transposon Tn7. Curr. Top. Microbiol. Immunol. 204: 27-48.

Devine, S. E. and Boeke, J. D., Nucleic Acids Research, 1994, 22(18): 3765-3772.

Goldhaber-Gordon et al., J Biol Chem. 277 (2002) 7703-7712

Haapa, S. et al., Nucleic Acids Research, vol. 27, No. 13, 1999, pp. 2777-2784

Ichikawa H. and Ohtsubo E., J. Biol. Chem., 1990, 265(31): 18829-32.

Kaufman P. and Rio D. C. 1992. Cell, 69(1): 27-39.

Kleckner N., Chalmers R. M., Kwon D., Sakai J. and Bolland S. Tn10 and IS10 Transposition and chromosome rearrangements: mechanism and regulation in vivo and in vitro. Curr. Top. Microbiol. Immunol., 1996, 204: 49-82.

Lampe D. J., Churchill M. E. A. and Robertson H. M., EMBO J., 1996, 15(19): 5470-5479.

Ohtsubo E. & Sekine Y. Bacterial insertion sequences. Curr. Top. Microbiol. Immunol., 1996, 204:1-26.

Park B. T., Jeong M. H. and Kim B. H., Taehan Misaengmul Hakhoechi, 1992, 27(4): 381-9.

Savilahti, H. and K. Mizuuchi. 1996. Mu transpositional recombination: donor DNA cleavage and strand transfer in trans by the Mu transposase. Cell 85:271-280.

Savilahti, H., P. A. Rice, and K. Mizuuchi. 1995. The phage Mu transpososome core: DNA requirements for assembly and function. EMBO J. 14:4893-4903.

Varmus H and Brown. P. A. 1989. Retroviruses, in Mobile DNA. Berg D. E. and Howe M. eds. American Society for Microbiology, Washington D.C. pp. 53-108.

Vos J. C., Baere I. And Plasterk R. H. A., Genes Dev., 1996, 10(6): 755-61.

Applicants incorporate by reference the material contained in the accompanying computer readable Sequence Listing identified as Sequence Listing_ST25.txt, having a file creation date of Jul. 17, 2012 1:49 P.M. and file size of 1.98 KB.

What is claimed is:

1. A modified transposon nucleic acid comprising a MuA transposon end sequence comprising the nucleotide sequence of SEQ ID NO:5.

2. The modified transposon nucleic acid of claim 1 where the transposon end sequence further comprises a MuA transposase.

3. A DNA sequencing kit comprising a transposon nucleic acid of claim 1.

4. The DNA sequencing kit of claim 3, further comprising a MuA transposase.

5. The modified transposon nucleic acid of claim 1, further comprising a MuA transposase and a target DNA.

6. An in vitro method for generating a DNA library, the method comprising
   a) incubating a transposon complex comprising a modified transposon nucleic acid of claim 1 and a MuA transposase with a target DNA of interest under conditions for carrying out a transposition reaction, where the modified transposon nucleic acid comprises a transposon end sequence recognizable by the MuA transposase, and where the transposition reaction results in fragmentation of the target DNA, and
   b) incorporating the transposon end into the 5' end of the fragmented target DNA to generate a fragmented target DNA, and
   c) contacting the fragmented target DNA with a DNA polymerase having 5'-3' exonuclease or strand displacement activity to generate a fully double-stranded target DNA.

7. The method of claim 6 further comprising amplifying the fragmented target DNA in an amplification reaction using a first and second oligonucleotide primer which is complementary to the transposon end in the 5' ends of the fragmented target DNA, where the first and second oligonucleotide primer optionally comprise 5' adaptor tails which are not complementary to the transposon end in the 5' ends of the fragmented target DNA.

8. The method of claim 6 further comprising the steps of denaturating the fully double-stranded target DNA to produce single stranded DNA, and amplyfing the single stranded DNA.

9. The method of claim 6 where the transposon end further comprises a cleavage site.

10. The method of claim 9 further comprising a step of incubating the fragmented target DNA with an enzyme specific to the cleavage site so that the transposon ends incorporated into the fragmented target DNA are cleaved at the cleavage site.

11. The method of claim 10 where the enzyme is an N-glycosylase or a restriction enzyme.

12. The method of claim 11 where the N-glycosylase is uracil-N-glycosylase.

13. The method of claim 11 where the restriction enzyme is a methylation specific restriction enzyme.

14. The method of claim 7 where the 5' adaptor tail of the first and/or second oligonucleotide primers comprise a tag selected from the group consisting of an amplification tag, a sequencing tag, a detection tag, and combinations thereof.

15. The method of claim 7 where the 5' adaptor tail of the first and/or second oligonucleotide primers comprise a sequencing tag, and the method further comprises denaturating the amplification products to produce a single stranded DNA, annealing the single stranded DNA to a solid support coated with an oligonucleotide complementary to the sequencing tag, and performing a DNA sequencing reaction using the single stranded DNA immobilized to a solid support as a template.

16. The method of claim 6 further comprising a step of sequencing the fragmented DNA so that the calibration sequence is read before the sequence of target DNA.

* * * * *

UNITED STATES PATENT AND TRADEMARK OFFICE
CERTIFICATE OF CORRECTION

PATENT NO. : 9,834,811 B2  
APPLICATION NO. : 14/836248  
DATED : December 5, 2017  
INVENTOR(S) : Ian Kavanagh et al.

Page 1 of 2

It is certified that error appears in the above-identified patent and that said Letters Patent is hereby corrected as shown below:

In the Claims

Claims 1-16 should read:
-- 1. A modified transposon nucleic acid comprising a MuA transposon end sequence comprising the nucleotide sequence of SEQ ID NO:5.

2. The modified transposon nucleic acid of claim 1 where the transposon end sequence further comprises a MuA transposase.

3. An in vitro method for generating a DNA library, the method comprising
a) incubating a transposon complex comprising a modified transposon nucleic acid of claim 1 and a MuA transposase with a target DNA of interest under conditions for carrying out a transposition reaction, where the modified transposon nucleic acid comprises a transposon end sequence recognizable by the MuA transposase, and where the transposition reaction results in fragmentation of the target DNA, and
b) incorporating the transposon end into the 5' end of the fragmented target DNA to generate a fragmented target DNA, and
c) contacting the fragmented target DNA with a DNA polymerase having 5'-3' exonuclease or strand displacement activity to generate a fully double-stranded target DNA.

4. The method of claim 3 further comprising amplifying the fragmented target DNA in an amplification reaction using a first and second oligonucleotide primer which is complementary to the transposon end in the 5' ends of the fragmented target DNA, where the first and second oligonucleotide primer optionally comprise 5' adaptor tails which are not complementary to the transposon end in the 5' ends of the fragmented target DNA.

5. The method of claim 3 further comprising the steps of denaturating the fully double-stranded target DNA to produce single stranded DNA, and amplyfing the single stranded DNA.

6. The method of claim 3 where the transposon end further comprises a cleavage site.

Signed and Sealed this
Fifth Day of June, 2018

Andrei Iancu
*Director of the United States Patent and Trademark Office*

7. The method of claim 6 further comprising a step of incubating the fragmented target DNA with an enzyme specific to the cleavage site so that the transposon ends incorporated into the fragmented target DNA are cleaved at the cleavage site.

8. The method of claim 7 where the enzyme is an N-glycosylase or a restriction enzyme.

9. The method of claim 8 where the N-glycosylase is uracil-N-glycosylase.

10. The method of claim 8 where the restriction enzyme is a methylation specific restriction enzyme.

11. The method of claim 4 where the 5' adaptor tail of the first and/or second oligonucleotide primers comprise a tag selected from the group consisting of an amplification tag, a sequencing tag, a detection tag, and combinations thereof.

12. The method of claim 4 where the 5' adaptor tail of the first and/or second oligonucleotide primers comprise a sequencing tag, and the method further comprises denaturing the amplification products to produce a single stranded DNA, annealing the single stranded DNA to a solid support coated with an oligonucleotide complementary to the sequencing tag, and performing a DNA sequencing reaction using the single stranded DNA immobilized to a solid support as a template.

13. The method of claim 3 further comprising a step of sequencing the fragmented DNA so that the calibration sequence is read before the sequence of target DNA.

14. A DNA sequencing kit comprising a transposon nucleic acid of claim 1.

15. The DNA sequencing kit of claim 14, further comprising a MuA transposase.

16. The modified transposon nucleic acid of claim 1, further comprising a MuA transposase and a target DNA. --